United States Patent [19]

Pamer

[11] 4,418,231
[45] Nov. 29, 1983

[54] CORROSION INHIBITED SOLVENT COMPOSITIONS

[75] Inventor: Steven E. Pamer, Rittman, Ohio

[73] Assignee: PPG Industries, Inc., Pittsburgh, Pa.

[21] Appl. No.: 290,770

[22] Filed: Aug. 7, 1981

[51] Int. Cl.$^3$ .................. C07C 17/42; C23G 5/02
[52] U.S. Cl. .................. 570/115; 252/364; 549/29; 570/111
[58] Field of Search .............. 570/111, 115; 252/364

[56] References Cited

U.S. PATENT DOCUMENTS

| Re. 26,025 | 5/1966 | Kauder | 260/652.5 |
|---|---|---|---|
| 3,008,999 | 11/1961 | Kauder | 260/652.5 |
| 3,043,888 | 7/1962 | Pray et al. | 260/652.5 |
| 3,099,694 | 7/1963 | Grammer et al. | 260/652.5 |
| 3,113,154 | 12/1963 | Trotter | 260/652.5 |
| 3,113,155 | 12/1963 | Sims | 260/652.5 |
| 3,113,156 | 12/1963 | Sims | 260/652.5 |
| 3,128,315 | 4/1964 | Hardies | 260/652.5 |
| 3,238,137 | 3/1966 | Grammer et al. | 252/171 |
| 3,251,891 | 5/1966 | Cormany et al. | 260/652.5 |
| 3,265,747 | 8/1966 | Cormany et al. | 260/652.5 |
| 3,326,988 | 6/1967 | Stack | 260/652.5 |
| 3,326,989 | 6/1967 | Cormany et al. | 260/652.5 |
| 3,397,148 | 8/1968 | Grammer et al. | 252/171 |
| 3,431,281 | 3/1969 | Sawaya | 260/340.9 |
| 3,499,047 | 3/1970 | Cormany et al. | 260/652.5 |
| 3,532,761 | 10/1970 | Manner | 260/652.5 |
| 3,583,944 | 6/1971 | Sawaya et al. | 260/75 T |
| 3,905,999 | 9/1975 | Krutak | 260/319.1 |
| 3,943,132 | 3/1976 | Schirmann et al. | 260/247.5 R |
| 4,026,956 | 5/1977 | Manner | 260/652.5 R |
| 4,096,187 | 6/1978 | Bonfield et al. | 260/601 H |
| 4,237,069 | 12/1980 | Ulmer et al. | 564/258 |

FOREIGN PATENT DOCUMENTS 739022 10/1955 United Kingdom .

OTHER PUBLICATIONS

S. M. McElvain and M. J. Curry, "Ketene Acetals. XIX 2–Methylene–1,3–Dioxolanes and 1,3–Dioxolanes", *Journal of the American Chemical Society*, vol. 70, pp. 3781–3786, (Nov., 1948).

*Primary Examiner*—Allan Lieberman
*Attorney, Agent, or Firm*—George D. Morris

[57] ABSTRACT

2-Alkylidene-1,3-dioxolanes and 2-(1-alkylalkylidene)-1,3-dioxolanes are employed as acid acceptors in methylchloroform, trichloroethylene or mixtures thereof. The preferred acid acceptor is 2-methylene-1,3-dioxolane.

In another aspect of the invention, aliphatic aldehyde hydrazone is employed to stabilize 2-alkylidene-1,3-dioxolane and 2-(1-alkylalkylidene)-1,3-dioxolane. The preferred aliphatic aldehyde hydrazone is acetaldehyde dimethylhydrazone.

11 Claims, No Drawings

CORROSION INHIBITED SOLVENT COMPOSITIONS

BACKGROUND OF THE INVENTION

Methylchloroform (i.e., 1,1,1-trichloroethane) and trichloroethylene are industrial solvents widely used for degreasing. Their usefulness in degreasing metals, especially light metals such as aluminum, is restricted because of their high degree of sensitivity to decomposition in the presence of aluminum. This sensitivity is particularly acute when methylchloroform and/or trichloroethylene contacts aluminum containing freshly exposed surfaces such as when the aluminum is scratched while submerged in the chlorinated hydrocarbon. Without the protection offered by formulating with the appropriate additive under such circumstances, methylchloroform and trichloroethylene decompose to various undesirable reaction products. Methylchloroform in particular decomposes into an unmanageable black tarry mass in a relatively brief period. It is thus commonplace to add to solvent compositions containing methylchloroform and/or trichloroethylene certain additives to protect against decomposition of these materials, including that type of decomposition which is particularly acute in the presence of freshly exposed surfaces of aluminum.

Even though stabilized with appropriate additives, methylchloroform and trichloroethylene do decompose, albeit at a much reduced rate as compared to solvent compositions not containing the additives. Unfortunately, whether stabilized with such additives or not, the decomposition products of methylchloroform and trichloroethylene include acid species which are corrosive to many of the metals being degreased. An acid species which is particularly troublesome is hydrogen chloride. It has accordingly been the usual practice to add an acid acceptor to methylchloroform and/or trichloroethylene to remove acidic species from the system. Epoxy compounds such as the 1,2 and 2,3 isomers of butylene oxide have been used for this purpose. Not only must the acid acceptor be compatible with other materials in the solvent system and perform its acid accepting function, but the products of the acid accepting reaction must be stable, compatible and essentially non-corrosive toward metals being degreased. These constraints impose considerable limitations on the types of acid acceptors which may be used in these chlorinated hydrocarbon systems.

THE INVENTION

It has now been found that 2-alkylidene-1,3-dioxolanes and 2-(1-alkylalkylidene)-1,3-dioxolanes are effective as acid acceptors in methylchloroform and/or trichloroethylene solvent compositions.

Accordingly, the invention contemplates solvent composition comprising (a) a member selected from the group consisting of methylchloroform, trichloroethylene and a mixture thereof, and (b) a corrosion inhibiting amount of acid acceptor represented by the structural formula

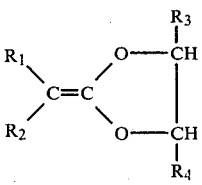

wherein $R_1$ and $R_2$ are each independently hydrogen, methyl or ethyl and wherein $R_3$ and $R_4$ are each independently hydrogen or alkyl containing from 1 to about 6 carbon atoms. $R_1$ and $R_2$ are preferably both hydrogen. When $R_3$ and/or $R_4$ are alkyl, they may be straight or branched, but if branched, they should not be so highly branched as to significantly hinder the formation of stable products of the acid accepting reaction. Straight alkyl groups are preferred. Typically, $R_3$ and $R_4$ are each independently hydrogen or lower alkyl containing from 1 to 4 carbon atoms. Preferably, $R_3$ and $R_4$ are each independently hydrogen, methyl or ethyl. It is particularly preferred that $R_3$ and $R_4$ both be hydrogen.

Examples of acid acceptors which are satisfactory for use in the invention include 2-methylene-1,3-dioxolane, 2-methylene-4-methyl-1,3-dioxolane, 2-methylene-4-ethyl-1,3-dioxolane, 2-methylene-4-propyl-1,3-dioxolane, 2-methylene-4-butyl-1,3-dioxolane, 2-methylene-4-isobutyl-1,3-dioxolane, 2-methylene-4-hexyl-1,3-dioxolane, 2-methylene-4,5-dimethyl-1,3-dioxolane, 2-methylene-4,5-diethyl-1,3-dioxolane, 2-methylene-4,5,-dipropyl-1,3-dioxolane, 2-methylene-4,5-dibutyl-1,3-dioxolane, 2-methylene-4,5-diisobutyl-1,3-dioxolane, 2-methylene-4-methyl-5-ethyl-1,3-dioxolane, 2-methylene-4-methyl-5-isobutyl-1,3-dioxolane, 2-methylene-4-butyl-5-isobutyl-1,3-dioxolane, 2-ethylidene-1,3-dioxolane, 2-ethylidene-4-methyl-1,3-dioxolane, 2-ethylidene-4-ethyl-1,3-dioxolane, 2-ethylidene-4-hexyl-1,3-dioxolane, 2-ethylidene-4,5-dimethyl-1,3-dioxolane, 2-isopropylidene-1,3-dioxolane, 2-isopropylidene-4-methyl-1,3-dioxolane, 2-isopropylidene-4-ethyl-1,3-dioxolane, 2-isopropylidene-4,5-dimethyl-1,3-dioxolane, 2-(1-methylpropylidene)-1,3-dioxolane, 2-(1-methylpropylidene)-4-methyl-1,3-dioxolane, 2-(1-methylpropylidene)-4,5-dimethyl-1,3-dioxolane, 2-(1-ethylpropylidene)-1,3-dioxolane, 2-(1-ethylpropylidene)-4-methyl-1,3-dioxolane, 2-(1-ethylpropylidene)-4,5-dimethyl-1,3-dioxolane, and 2-(1-ethylpropylidene)-4-methyl-5-ethyl-1,3-dioxolane. The especially preferred acid acceptor is 2-methylene-1,3-dioxolane. Only one or a mixture of any of the various unsaturated 1,3-dioxolane compounds of Formula I may be used as desired.

The amounts of the various components present in the compositions of the invention are subject to wide varation. Typically the methylchloroform, trichloroethylene or a mixture thereof constitutes from about 85 percent to about 99.99 percent by weight of the solvent composition. From about 94 percent to about 99.6 percent by weight is preferred. While mixtures containing significant amounts of both methylchloroform and trichloroethylene may be employed, the usual practice is to use either methylchloroform or trichloroethylene.

Chlorinated hydrocarbons other than methylchloroform and/or trichloroethylene may be present in the solvent compositions of the invention, but if present they ordinarily constitute a minor amount, e.g., less than about 20 percent by weight, of such solvent compositions. In some cases one or more of these other chlorinated hydrocarbons may be added in significant amounts for a particular purpose, but normally they are present, if at all, as impurities in low amounts typical of the commercial manufacture of methylchloroform or trichloroethylene.

The concentration of the 2-alkylidene-1,3-dioxolane and/or 2-(1-alkylalkylidene)-1,3-dioxolane material, whether or not alkyl substituted on the ring, in the solvent composition is also subject to wide variation. It ordinarily constitutes from about 0.01 percent to about 10 percent by weight of the methylchloroform, trichloroethylene or mixtures thereof present in the solvent composition. From about 0.2 percent to about 1 percent by weight is preferred.

The unsaturated compounds represented by Formula I are not the only additives which may be incorporated in the solvent compositions of the invention. Other additives may optionally also be included.

Besides the compounds of Formula I, other 1,3-dioxolanes may be included. These include saturated 1,3-dioxolanes containing up to two alkyl substituents, each of the alkyl substituents having from 1 to 2 carbon atoms, such as 1,3-dioxolane, 4-methyl-1,3-dioxolane, 2-ethyl-1,3-dioxolane, 2,2-dimethyl-1,3-dioxolane, 4,4-diethyl-1,3-dioxolane, 2,4-dimethyl-1,3-dioxolane, 2-methyl-4-ethyl-1,3-dioxolane and the like (including those enumerated in column 6 of U.S. Pat. No. 3,397,148, the disclosure of which is incorporated herein by reference). Generally, those 1,3-dioxolanes normally boiling within the range of 50° C. to about 120° C., more ideally in the range of 65° to 85° C. are preferable. The preferred saturated dioxolane is 1,3-dioxolane.

Nitroalkanes having from 1 to about 3 carbon atoms may be employed. Examples include nitromethane, nitroethane, 1-nitropropane and 2-nitropropane. Nitromethane is preferred. One nitroalkane or a mixture of nitroalkanes may be used as desired.

One or more other acid accepting compounds may also be included. These may be exemplified by epoxide compounds such as 1,2-butylene oxide, 2,3-butylene oxide, epichlorohydrin, glycidol, propylene oxide, cis-2,3-pentene oxide, 2-methyl-2,3-epoxybutane, 1,2-epoxycyclopentane, 2,3-dimethyl-2,3-epoxybutane, 2-chloro-3,4-epoxybutane, 1-chloro-2,3-epoxybutane, styrene oxide, 1,2-epoxycyclohexane and the like. Preference is for saturated aliphatic monoepoxides containing from about 3 to about 8 carbon atoms, ideally from about 4 to about 6 carbon atoms, and saturated cycloaliphatic monoepoxides containing from about 6 to about 8 carbon atoms. Either or both of the butylene oxide isomers are especially preferred.

Additionally, the solvent compositions often may be improved by the incorporation therein of other additives including acetylenic alcohols, that is alkynols, and short chain aliphatic monohydric saturated alcohols. Useful acetylenic alcohols include those which contain from 3 to about 12 carbon atoms and a single triple bond. By way of illustration such acetylenic alcohols include 2-methyl-3-butyn-2-ol, propargyl alcohol, 2-butyn-1-ol, 3-butyn-2-ol, 2,5-dimethyl-3-hexyn-2,5-diol, 3,6-dimethyl-4-octyn-3,6-diol and the like. The particular useful saturated monohydric alcohols have from 1 to about 8 carbon atoms among which may be mentioned the alkanols methanol, n-propanol, isopropanol, sec-butanol, t-butanol, n-butanol, isobutanol, t-amyl alcohol, hexanol, octanol and mixtures thereof. n-Propanol, isobutanol and t-butanol are preferred.

Aliphatic aldehyde hydrazones having from 1 to about 7 carbon atoms and with no aliphatic group having more than about 4 carbon atoms, may also optionally be included in the solvent compositions of the invention. Such aliphatic aldehyde hydrazones may be represented by the formula

wherein $R_5$, $R_6$ and $R_7$ may each independently be hydrogen or an aliphatic group, including saturated and unsaturated aliphatic groups, of from 1 to about 4 carbon atoms with the proviso that the aliphatic aldehyde hydrazone have from 1 to about 7 carbon atoms. For most of the aliphatic aldehyde hydrazones, the sum of the carbon atoms in the aliphatic groups is preferably not in excess of 5. Often the aliphatic groups of the aliphatic aldehyde hydrazone are alkyl groups. Aliphatic aldehyde hydrazones are described in U.S. Pat. No. 3,043,888 and U.S. Pat. No. 4,026,956, the disclosures of which are incorporated herein by reference. Examples of aliphatic aldehyde hydrazones include formaldehyde hydrazone, formaldehyde diethyl hydrazone, formaldehyde dimethyl hydrazone, formaldehyde methyl ethyl hydrazone, acetaldehyde methyl hydrazone, acetaldehyde methyl ethyl hydrazone, formaldehyde propyl hydrazone, formaldehyde isopropyl hydrazone, n-butyraldehyde dimethyl hydrazone and propionaldehyde hydrazone. Acetaldehyde dimethylhydrazone is preferred. One or a mixture of any of the various aliphatic aldehyde hydrazones may be used as desired.

Another class of additives which may be used are aromatic compounds having a phenolic hydroxyl group linked directly to a ring carbon such as phenol, thymol, catechol, para-cresol, guaicol, methyl salicylate, eugenol, isoeugenol, hydroquinone monomethyl ether, 2,6-di-tert-butyl-p-cresol and like phenols having a normal boiling temperature in the range of from about 180° C. to about 250° C. One phenol or a mixture of phenols may be used when desired.

A wide variety of amines may also be present. Among the typical amines are diethylamine, triethylamine, dipropylamine, tripropylamine, triisopropylamine, dibutylamine, di-sec-butylamine, di-isobutylamine, di-isopropylamine, diethanolamine, morpholine, N-methylmorpholine, triethanolamine, beta-picoline, pyridine and aniline. Other nitrogenous additives which may be present include pyrroles such as N-methylpyrrole. One amine or a mixture of amines may be used as desired.

Other optional additives which often impart desirable properties to the solvent compositions of the invention include 1,4-dioxane; trioxane; tetrahydrofuran; alkanoic acid esters such as methyl alpha-hydroxy isobutyrate, ethyl acetate, etc.; ketones such as acetone, methyl ethyl ketone, methyl isopropyl ketone, diethyl ketone, 2-hexanone, methyl tert-butyl ketone, acetyl acetone, mesityl oxide, phorone, cyclohexanone, acetophenone, etc.; nitriles exemplified by acetonitrile, propionitrile and acrylonitrile; ketols such as acetol, 4-hydroxy-2-butanone and 5-hydroxy-3-pentanone; dialkyl sulfoxides such as dimethyl sulfoxide, di-isopropyl sulfoxide and methyl ethyl sulfoxide; organic nitrates such as isopropyl nitrate, ethyl nitrate and methyl nitrate; dimethoxymethane; dialkyl ethers of diols (notably the dialkyl ethers specifically numerated in U.S. Pat. No. 3,128,315 exemplified by dimethoxyethane; the disclosure of U.S. Pat. No. 3,128,315 is incorporated herein by reference). Liquid hydrocarbons (aliphatic and aromatic) can be included. For example, toluene, n-hexane, pentane or like hydrocarbon is often a useful component in providing an all-purpose chlorinated solvent composition.

The total concentration of all stabilizer additives, including the 2-alkylidene-1,3-dioxolane and 2-(1-alkylalkylidene)-1,3-dioxolane compounds as well as any optional additives, incorporated with methylchloroform, trichloroethylene, or a mixture thereof should generally be in the range of from about 0.01 percent to about 15 percent by weight of the solvent composition. Preferably the total concentration of all stabilizer additives is in the range of from about 0.4 percent to about 6 percent by weight of the solvent composition. In those solvent compositions containing a plurality of additives, it is generally good practice to minimize the concentration of any one particular additive recognizing the impact upon total additive concentration the other additives impose. Rarely will the concentration of any one additive exceed 5 percent by weight; more aptly it will be in the range of from about 0.1 weight percent to about 3½ weight percent.

The compositions of the invention are conveniently prepared by admixing the various ingredients.

The compounds of Formula I may be prepared by dehydrohalogenation of the corresponding 2-(1-haloalkyl)-1,3-dioxolane represented by the formula

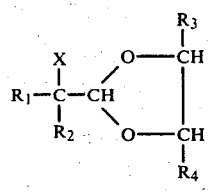
(III)

wherein $R_1$, $R_2$, $R_3$ and $R_4$ are as previously described with respect to Formula I and X is chloro or bromo. The dehydrohalogenation may be accomplished, for example, by potassium tert-butoxide in tert-butyl alcohol; see McElvain and Curry, *Journal of the American Chemical Society*, volume 70 (November 1948), pages 3781–3786. Dehydrohalogenation is preferably accomplished by sodium amide or potassium amide in anhydrous liquid ammonia. The sodium amide or the potassium amide may conveniently be prepared in situ from metallic sodium or metallic potassium. See U.S. Pat. No. 3,431,281, the disclosure of which is incorporated herein by reference.

The compounds of Formula III may be prepared by reacting the corresponding haloacetal represented by the formula.

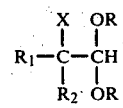
(IV)

with an alkanediol represented by the structural formula

where $R_1$, $R_2$, $R_3$ and $R_4$ are as previously described with respect to Formula I, R is lower alkyl, and X is chloro or bromo. Typically, R is methyl or ethyl. An acid catalyst or an acidic cation exchange resin and elevated temperatures are generally employed in the reaction. Examples of suitable alkanediols include 1,2-ethanediol, 1,2-propanediol, 1,2-butanediol, 1,2-pentanediol, 1,2-hexanediol, 1,2-octanediol, 2,3-butanediol, 3,4-hexanediol, 4,5-octanediol, 5,6-decanediol, 2,7-dimethyl-4,5-octanediol, 2,3-pentanediol, 5-methyl-2,3-hexanediol and 2-methyl-4,5-nonanediol.

The compounds of Formula IV may be prepared by reacting the corresponding haloaldehyde represented by the formula

with a lower alkanol represented by the formula

wherein $R_1$ and $R_2$ are as previously described with respect to Formula I, X is chloro or bromo and R is lower alkyl, usually methyl or ethyl. The reaction is conducted under conditions customarily associated with acetal formation. Examples of suitable Formula VI compounds include chloroacetaldehyde, 2-chloropropionaldehyde, 2-chlorobutyraldeyde 2-methyl-2-chloropropionaldehyde, 2-methyl-2-chlorobutyraldehyde, 2-ethyl-2-chlorobutyraldehyde and the corresponding 2-bromo analogs.

In another method, the compounds of Formula III may be prepared by reacting the corresponding haloaldehyde represented by Formula VI with an alkanediol of Formula V wherein $R_1$, $R_2$, $R_3$ and $R_4$ are as previously described with respect to Formula I and X is chloro or bromo. An acid catalyst or an acidic cation exchange resin and elevated temperatures are generally employed in the reaction. See British Patent Specification No. 739,022, the disclosure of which is incorporated herein by reference.

The unsaturated 1,3-dioxolane compounds of Formula I are ordinarily difficult to purify and store because they have a pronounced tendency to spontaneously polymerize. It has been discovered that the presence of a stabilizing amount of one or more aldehyde hydrazones serves to reduce the tendency of the Formula I compounds to spontaneously polymerize. Purification of these unsaturated 1,3-dioxolane compounds by distillation at reduced pressure is ordinarily accomplished with less spontaneous polymerization if the aldehyde hydrazone is present than when it is absent. Similarly, storage of the unsaturated 1,3-dioxolane compounds is usually accomplished with less spontaneous polymerization when the aldehyde hydrazone is present than when it is absent.

Accordingly, the invention contemplates a composition comprising (a) unsaturated 1,3-dioxolane represented by the structural formula of Formula I, above, wherein $R_1$ and $R_2$ are each independently hydrogen, methyl or ethyl and wherein $R_3$ and $R_4$ are each independently hydrogen or alkyl containing from 1 to about 6 carbon atoms, and (b) a stabilizing amount of aliphatic aldehyde hydrazone represented by the structural formula of Formula II wherein $R_5$, $R_6$ and $R_7$ are each independently hydrogen or an aliphatic group, including saturated and unsaturated aliphatic groups with the proviso that the aliphatic aldehyde hydrazone has from 1 to 7 carbon atoms. The earlier discussion respecting $R_1$, $R_2$, $R_3$ and $R_4$ is applicable here, as are the examples of 2-alkylidene-1,3-dioxolane and 2-(1-alkylalkylidene)-1,3-dioxolane compounds previously set forth. The preferred Formula I compound is 2-methylene-1,3-dioxolane. One unsaturated 1,3-dioxolane or a mixture of unsaturated 1,3-dioxolanes may be used as desired. Similarly, the earlier discussion respecting $R_5$, $R_6$ and $R_7$ is applicable here, as are the examples of aliphatic aldehyde hydrazones previously set forth. The preferred aliphatic aldehyde hydrazone is acetaldehyde dimethylhydrazone. One aliphatic aldehyde hydrazone or a mixture of such compounds may be used as desired. The preferred stabilizing material is acetaldehyde dimethylhydrazone.

The concentration of the aliphatic aldehyde hydrazone in the composition is subject to wide variation. It ordinarily constitutes from about 0.1 percent to about 10 percent by weight of the Formula I compounds present. From about 0.3 percent to about 5 percent by weight is preferred. The stabilized unsaturated 1,3-dioxolane compositions may be produced by admixing the various ingredients.

In the illustrative examples which follow, all parts are parts by weight and percentages are percent by weight unless otherwise specified.

The pH/titer tests are conducted as follows. A dilute sodium chloride solution is prepared by dissolving 1 gram sodium chloride in 1 gallon neutral distilled water. A 25 milliliter sample of the solvent composition to be tested is placed in a 250 milliliter beaker containing 75 milliliters of the dilute sodium chloride solution. The charged materials are mechanically stirred while the pH is determined using a pH meter employing a glass electrode and a calomel electrode. Depending on the pH observed, the sample is titrated with 0.01 N sodium hydroxide or 0.01 N hydrochloric acid until a neutral value of pH 7 is obtained. The material is considered to be neutral when it retains a pH in the range of from 7.0 to 7.3 for at least 30 seconds. The titer is reported as the milliliters of 0.01 N sodium hydroxide or 0.01 N hydrochloric acid used to obtain neutrality.

The blender agitation test is conducted as follows. Forty grams of aluminum chips (7075-T6) is placed in the one-quart glass jar of a Model 700 one-speed Waring Blender. After adding 210 milliliters of the solvent composition to be tested, the solvent composition and the aluminum chips are agitated by the blender until decomposition occurs or agitation has proceeded for 10 minutes. The appearance of the solvent as observed immediately after blending, after standing 30 minutes and after filtering is generally reported. The pH/titer and APHA color of the filtrate are measured.

The aluminum turnings-cutting oil reflux test is conducted as follows. A 500 milliliter Erlenmeyer flask having a ground glass outer joint is tared and charged with 20 grams Houghton 3105 cutting oil, 300 milliliters of the solvent to be tested, 45 milliliters Ashland 330 solvent (a neutral oil), 7.5 milliliters Shell K-13 oil, 8 grams 2024 alloy aluminum chips, 8 grams 7075 alloy aluminum chips, several silica boiling chips, and three ½ inch by 1¼ inch by 1/16 inch mild steel strips which have been etched with concentrated hydrochloric acid, rinsed with water, dried, buffed with a wire wheel and rinsed with acetone. A copper wire is run through a water-cooled condenser and bent over the top rim. A 3/32 inch hole is drilled in a buffed 2024 alloy aluminum strip measuring ½ inch by 3 inches. The aluminum strip is rinsed with acetone and hooked to the copper wire so that condensate will run down the suspended strip. The contents of the flask are thoroughly mixed and a 50 milliliter portion of the solvent and oil mixture is removed to a tared graduate. The weight of the mixture is recorded and the density is calculated. The flask joint is connected to the condenser using a polytetrafluoroethylene sleeve. A hot plate is placed under the flask and the time at which refluxing begins is noted. Using a hypodermic syringe and needle, 50 milliliter samples of liquid are withdrawn through the condenser after refluxing 24 hours and 48 hours, respectively. After refluxing a total of 168 hours, heating is terminated and a sample of the liquid is taken. The samples are tested for pH/titer.

The blade aluminum scratch test is conducted as follows. A scribe is made from a 5 to 7 inch length of 5/16 inch diameter stainless steel rod. One end is ground to a knife edge so that the edge is at a 45 degree angle to the axis of the rod. The other end is inserted into a rubber stopper or a wooden file handle. A 2 ounce wide-mouthed bottle is clamped to a table. A 2024 alloy aluminum test strip measuring ½ inch by 1⅜ inch by 1/16 inch is placed in the bottle. Sufficient solvent composition is added to cover the entire strip. Three scratches are slowly made the length of the strip with the scribe blade while maximum pressure is exerted on the scribe by the operator. The sample is then allowed to stand undisturbed for 24 hours with the bottle cap lying (not tightened) on the top of the bottle. A numerical value is assigned for the appearance of the solvent, precipitate and strip after 24 hours and an average figure is reported. The rating system is shown in Table 1. In the case of complete solvent decomposition, the formulation is given a rating of 10. The scribe is resharpened with a file after each test.

TABLE 1

| Blade Aluminum Scratch Test Rating System | | | | | |
|---|---|---|---|---|---|
| Solvent | | Precipitate or Haze | | Strip | |
| Color | Rating | Condition | Rating | Condition | Rating |
| Colorless | 1 | None | 1 | No scar or solid on strip | 1 |
| Slight color | 2 | Slight haze | 2 | Very sl. white solid in scratch | 2 |
| Yellow or med. amber | 3 | Haze and/or sl. ppt. | 3 | Sl. scar or solid in scratch | 3 |
| Dark amber | 4 | Precipitate | 4 | Scar | 4 |
| Black | 5 | Heavy precipitate | 5 | Enlarged scar | 5 |

The Federal Accelerated Oxidation test is described in Military Specification MIL-T-7003, Sept. 5, 1950 and O-T-634a, Apr. 17, 1956. A 500 milliliter Erlenmeyer flask having a ground glass joint is charged with 200 milliliters of the solvent to be tested. A ¼ inch by ¾ inch by 1/16 inch steel (SAE 1020 to 1040) strip is placed in the bottom of the flask. A ½ inch by 2 inch by 1/16 inch steel (SAE 1020 to 1040) strip is suspended by means of a copper wire running through a water-cooled condenser having ground glass joints such that when the condenser is mated to the flask, the latter steel strip is suspended above the surface of the liquid in the flask. An oxygen delivery tube is passed through the condenser to within ¼ inch of the bottom of the flask. A 150 watt frosted electric light bulb is positioned vertically within a polished plated steel sleeve having four vent holes near the bottom. A ¼ inch Transite board having a 3¼ inch hole is positioned on top of the sleeve with the hole over the light bulb. The flask is positioned on the board and over the hole. The bottom of the flask is about ½ inch from the top of the light bulb. Water is circulated through the condenser, the light bulb is switched on and oxygen is admitted through a bubble counter and the delivery tube at the rate of one bubble every 5 to 7 seconds. After 48 hours of continuous refluxing, the contents of the flask are allowed to cool to room temperature. A 25 milliliter sample of the liquid is removed and tested according to the pH/titer tests described above.

The mild steel reflux test is conducted as follows: A ½ inch by 4 inch by 1/16 inch mild steel strip which has been etched with concentrated hydrochloric acid, rinsed with water, dried, polished with a wire wheel and rinsed with acetone, is placed in a 500 milliliter Erlenmeyer flask having a ground glass joint. Next, 250 milliliters of the solvent to be tested is added to flask, resulting in immersion of about one-half of the steel strip. The flask is fitted with a water-cooled reflux condenser, placed on a hot plate and refluxed for 24 hours. The APHA color of the liquid is ascertained. A sample of the liquid is tested according to the pH/titer tests described above.

The standard stability test is conducted in apparatus used in the Federal Accelerated Oxidation test except that (1) the oxygen delivery tube (now an air delivery tube) passing through the condenser also passes through a two-hole rubber stopper located in the top of the condenser, (2) tubing passing through the second hole of the rubber stopper directs gases venting from the condenser through a normally empty safety trap and then through a trap containing 0.1 N silver nitrate solution acidified with nitric acid, and (3) the ¼ inch Transite board has a ¾ inch hole. A solution is prepared by admixing 87.5 parts by volume of the solvent to be tested and 12.5 parts by volume Houghton H-3105 drawing compound. The 500 milliliter Erlenmeyer flask is charged with 250 milliliters of the solution, 5 grams of mossy zinc and 5 grams aluminum turnings. Water is circulated through the condenser, the light bulb is switched on, and air is admitted through the bubble counter and the delivery tube at a rate of approximately one bubble per second. After 72 hours of continuous refluxing, the contents of the flask are allowed to cool to room temperature. A 25 milliliter sample of the liquid is removed and tested according to the pH/titer tests described above.

EXAMPLE I

A three-necked, three liter flask equipped with a mechanical stirrer, a temperature recorder, a solid carbon dioxide-acetone reflux condenser and a source of nitrogen is charged with 1184.3 grams (69.6 moles) liquid anhydrous ammonia. A small piece of metallic potassium and 1 gram ferric nitrate nonahydrate [Fe(NO$_3$)$_3$.9H$_2$O] are added sequentially. Over a period of 3 hours, 59 grams (1.5 gram-atoms) metallic potassium is added. The resulting potassium amide/ammonia mixture is stirred for 30 minutes. While passing a slow stream of nitrogen through the addition funnel into the flask and out the condenser, 213.6 grams (1.74 moles) 2-chloromethyl-1,3-dioxolane is added dropwise. Upon completion of the addition, the reaction mixture is refluxed about 12 hours. The ammonia is then allowed to escape. To the remaining material is added 3.3 milliliters of a 40 percent solution of acetaldehyde dimethylhydrazone in trichloroethylene. The product is separated by vacuum distillation through a short Vigreaux column at an absolute pressure of 43 millimeters of mercury. Analysis by nuclear magnetic resonance spectroscopy shows the product to be 2-methylene-1,3-dioxolane of 80 to 90 percent purity, with the main impurity being 2-chloromethyl-1,3-dioxolane. The product polymerizes quite rapidly upon exposure to the air, but it could be stored under nitrogen in a household freezer for short periods of time before polymerization is observed.

EXAMPLE II

A three-necked, three liter flask is equipped with a mechanical stirrer, a 500 milliliter pressure equalizing addition funnel with a stopcock in the side arm and a Claisen adapter. One end of a stopcock is inserted in the straight tube of the Claisen adapter and a serum cap is affixed to the other end of the stopcock. A Friedrichs condenser is inserted in the parallel arm of the Claisen adapter. In the top joint of the Friedrichs condenser is inserted an adapter with a stopcock. This adapter is connected to a drying tube filled with calcium sulfate. The Friedrichs condenser is cooled by methanol circulating through a refrigerant loop. This loop runs, in the direction of the circulating methanol, from the outlet of the coolant side of the Friedrichs condenser to a tee in which is inserted a thermometer for measuring the temperature of the methanol, to a methanol reservoir, to a centrifugal pump, to a copper coil immersed in an insulated container filled with a mixture of solid carbon dioxide and acetone, and thence to the inlet of the coolant side of the Friedrichs condenser.

The reaction system is purged with nitrogen and the circulating methanol is cooled to the minimum stable temperature allowed by the system. Approximately 1245 grams (73.1 moles) of liquid ammonia is added to the flask. A small piece of metallic potassium and 1 gram of ferric nitrate nonahydrate are added sequentially. Over a period of about 3¼ hours, small pieces of metallic potassium are intermittently added while the refrigerant temperature is in the range of from about $-70°$ C. to about $-67°$ C. The total amount of metallic potassium added is 72 grams (1.84 gram-atoms). While passing a slow stream of nitrogen through the addition funnel into the flask and out the condenser, 225.7 grams (1.84 moles) 2-chloromethyl-1,3-dioxolane is added dropwise over a period of 83 minutes and is completed at 5:03 p.m. Stirring is continued. At 5:25 p.m. and 6:10 p.m. the refrigerant temperature is $-65°$ C. At 9:15 p.m. the solid carbon dioxide and acetone bath is replenished for the last time. At 8:10 a.m. the next morning there is no more solid carbon dioxide in the cooling bath and the refrigerant temperature is $-49°$ C. At 8:53 a.m. the temperature of the refrigerant is $-33°$ C. At this time a very slow nitrogen purge is started through the addition funnel. At 9:15 a.m. the refrigerant temperature is $-23°$ C. and the centrifugal pump for the refrigerant is turned off. At 10:20 to 10:25 a.m., 3.5 milliliters of a 40% solution of acetaldehyde dimethylhydrazone in trichloroethylene is added using a syringe and a long needle inserted through the rubber serum cap. Venting of ammonia by the slow nitrogen purge without external warming of the flask is continued until the next morning, at which time a considerable amount of solid precipitate is observed. While maintaining a slow nitrogen purge, the Friedrichs condenser and the Claisen adapter are replaced with a nitrogen purge adapter. The addition funnel is replaced with an 11 inch Vigereaux distillation column, distillation head and thermometer, condenser, a vacuum distillation adapter, and a 300 milliliter 2-necked receiver flask. A rubber serum cap is attached to the remaining neck of the receiver, and the nitrogen purge adapter on the three-liter flask is replaced with a glass stopper.

During distillation, the reaction flask is heated with an oil bath, the condenser is cooled with water circulated through an ice and water bath by a submersible pump, and the receiving flask is cooled by liquid nitrogen in a Dewar flask. Using a conventional vacuum system and associated hardware, distillation is conducted at an absolute pressure of 17 millimeters of mercury for about 2 hours while the temperature at the distillation head is in the range of 23° C. to 39° C. The system is returned to atmospheric pressure with nitrogen. To the 33.6 grams of frozen distillate which has been collected, is added 33.6 grams methylchloroform. The resulting first solution is stored in a freezer. Analysis by nuclear magnetic resonance spectroscopy shows the first solution to contain about 43 percent 2-methylene-1,3-dioxolane, about 51 percent methylchloroform and about 6 percent 2-chloromethyl-1,3-dioxolane.

In a similar manner, distillation of the remaining contents of the reaction flask is resumed, but during the distillation the absolute pressure is reduced from the initial 20 millimeters of mercury to 4 millimeters of mercury. To the frozen distillate collected is added 53.1 grams methylchloroform. The resulting second solution is stored in a freezer. Analysis by nuclear magnetic resonance spectroscopy shows the second solution to contain about 34 percent 2-methylene-1, 3-dioxolane, about 57 percent methylchloroform and about 9 percent 2-chloromethyl-1,3-dioxolane.

The appearance of the solutions after storage in a household freezer is shown in Table 2.

TABLE 2

| Solution | Storage Time (approximate) | Appearances |
|---|---|---|
| First | 2½ days | Clear and colorless; contains only a few specks of white solid. |
| Second | 2½ days | Cloudy. |
| First | 5 weeks | Cloudy; contains some finely divided white solid. |

EXAMPLE III

A first composition is prepared by admixing 1001.1 grams methylchloroform, 4.9 grams of an 80 percent 2-methylene-1,3-dioxolane composition wherein the chief impurity is 2-chloromethyl-1,3-dioxolane, 0.05 gram acetaldehyde dimethylhydrazone, 10.6 grams 1,3-dioxolane, 7.9 grams isobutanol, 7.9 grams methyl ethyl ketone, 21.1 grams nitromethane and 8.5 grams toluene.

An additive composition is prepared by admixing 21.9 grams of an 83 percent 2-methylene-1,3-dioxolane composition wherein the chief impurity is 2-chloromethyl-1,3-dioxolane and 22.4 grams methylchloroform.

A second composition is prepared by admixing 996.9 grams methylchloroform, 9.5 grams of the above additive composition, 0.05 gram acetaldehyde dimethylhydrazone, 10.6 grams 1,3-dioxolane, 8.0 grams isobutanol, 8.0 grams methyl ethyl ketone, 21.2 grams nitromethane and 8.5 grams toluene.

A conrol composition is prepared by admixing 1003.0 grams methylchloroform, 0.05 gram acetaldehyde dimethylhydrazone, 10.6 grams 1,3-dioxolane, 7.9 grams isobutanol, 7.9 grams methyl ethyl ketone, 21.2 grams nitromethane and 8.5 grams toluene.

The first composition, the second composition and the control composition are tested according to the pH/titer test, the blade aluminum scratch test and the blender agitation test. The results are shown in Table 3. The same compositions are also tested according to the aluminum turnings-cutting oil reflux test. The results are shown in Table 4.

TABLE 3

STABILITY TEST RESULTS

| COMPOSITION | pH/TITER INITIAL | BLADE ALUMINUM SCRATCH TEST (AVERAGE) | BLENDER AGITATION TEST | | | | |
|---|---|---|---|---|---|---|---|
| | | | pH/TITER | APHA COLOR | SOLVENT APPEARANCE AFTER: | | |
| | | | | | BLENDING | STANDING 30 MIN. | FILTERING |
| First | 6.8/0.2 | 4.2 | 4.2/2.8 | 4200 | Brown | Dk. brown | Amber |
| Second | 6.7/0.2 | 4.5(10*) | 4.7/2.9 | 2550 | Gray-green | Dk. amber | Amber |
| Control | 6.7/0.6 | 4.5 | 3.2/10.2 | 4380 | Dk. brown | Dk. brown | Dk. amber |

*1 out of 4 of the tests of this sample decomposed completely.

TABLE 4

RESULTS OF ALUMINUM TURNINGS-CUTTING OIL REFLUX TEST

| COMPO-SITION | pH/TITER AFTER | | | |
|---|---|---|---|---|
| | 0 HOURS | 24 HOURS | 48 HOURS | 168 HOURS |
| First | 6.1/1.0 | 6.5/0.5 | 6.7/0.3 | 6.6/0.4 |
| Second | 6.4/0.8 | 6.6/0.4 | 6.7/0.3 | 6.7/0.4 |
| Control | 5.4/1.5 | 3.9/3.0 | 3.3/7.8 | 2.9/15.4 |

EXAMPLE IV

A stabilized composition is prepared by admixing various additives with methylchloroform. The identity of the additives and their concentration expressed as percent by weight of the composition are:

| Nitromethane | 1.5 percent |
|---|---|
| 1,3-Dioxolane | 1.5 |
| 2-Methylene-1,3-dioxolane | 0.31 |
| Methyl Ethyl Ketone | 0.75 |
| Isobutanol | 0.75 |
| Toluene | 0.80 |

-continued

| Acetaldehyde Dimethylhydrazone | 0.005* |
|---|---|

*This concentration of acetaldehyde dimethylhydrazone does not include the amount of that material present in the 2-methylene-1,3-dioxolane used to prepare the formulation. Titration of 20-milliliter portions of the stabilized composition and the control composition with 0.1N HClO$_4$ in glacial acetic acid shows that the total concentration of acetaldehyde dimethylhydrazone in the stabilized composition is 2.5 times that in the control composition.

A first control composition is prepared in the same manner as above except that the 2-methylene-1,3-dioxolane is omitted.

The stabilized composition and the first control composition are tested according to the pH/titer test and the blender agitation test. The results are shown in Table 5. The same compositions are also tested according to the aluminum turnings-cutting oil reflux test. The results are shown in Table 6.

TABLE 5
STABILITY TEST RESULTS

| | | BLENDER AGITATION TEST | | |
|---|---|---|---|---|
| COMPOSITION | pH/TITER INITIAL | pH/TITER | APHA COLOR | SOLVENT APPEARANCE AFTER FILTERING |
| Stabilized | 7.30/<0.1 (pH drifts to 7.0) | 3.8/2.9 | 3000 | medium amber with a very slight haze |
| First Control | 6.7/0.3 | 2.9/10.8 | 3000 (dk. brwn.) | medium to dark amber with a very slight haze |

TABLE 6
RESULTS OF ALUMINUM TURNINGS-CUTTING OIL REFLUX TEST

| | REFLUX TIME, | | APPEARANCE AFTER 168 HOURS | | |
|---|---|---|---|---|---|
| COMPOSITION | HOURS | pH/TITER | SOLVENT | STEEL STRIPS | ALUMINUM CHIPS | ALUMINUM COUPON |
| Stabilized | 0 | 6.1/0.5 | amber | slight stains (iridescent) | clean | clean |
| | 24 | 6.5/0.4 | | | | |
| | 48 | 6.2/0.4 | | | | |
| | 168 | 6.4/0.5 | | | | |
| First Control | 0 | 4.6/1.3 | very dark amber | heavy brown stains (rust) | numerous black spot stains | heavy black and brown deposit on one side |
| | 24 | 3.3/5.2 | | | | |
| | 48 | 3.1/8.5 | | | | |
| | 168 | 2.9/13.2 | | | | |

To determine if the additional acetaldehyde dimethylhydrazone is responsible for the good performance of the stabilized composition as compared with the first control composition in the aluminum turnings-cutting oil reflux test, a second control composition is prepared which, except for the absence of the 2-methylene-1,3-dioxolane, has the same composition as the stabilized composition. The second control composition is then tested according to the aluminum turnings-cutting oil reflux test. The results are shown in Table 7.

TABLE 7
RESULTS OF ALUMINUM TURNINGS-CUTTING OIL REFLUX TEST

| | REFLUX TIME, | | APPEARANCE AFTER 168 HOURS | | |
|---|---|---|---|---|---|
| COMPOSITION | HOURS | pH/TITER | SOLVENT | STEEL STRIPS | ALUMINUM CHIPS | ALUMINUM COUPON |
| Second Control | 0 | 5.6/0.9 (pH drifts to 6.0) | very dark amber | heavy brown stains (rust) | a few small black spot stains | black deposit in upper corner; remainder was clean |
| | 24 | 3.2/6.9 | | | | |
| | 48 | 3.1/8.6 | | | | |
| | 168 | 3.1/8.8 | | | | |

EXAMPLE V

A control composition is prepared by admixing 2478.5 grams trichloroethylene containing 0.01 percent thymol, 0.25 gram acetaldehyde dimethylhydrazone, 3.1 grams n-propanol, 7.1 grams 1,2-butylene oxide and 1.0 gram cyclohexene oxide.

An additive composition is prepared by admixing 21.9 grams of an 83 percent 2-methylene-1,3-dioxolane composition wherein the main impurity is 2-chloromethyl-1,3-dioxolane, and 22.5 grams trichloroethylene.

A stabilized composition is prepared by admixing 798.0 grams of the control composition and 1.9 grams of the above additive composition.

The stabilized composition and the control composition are tested according to the pH/titer test, the Federal Accelerated Oxidation test and the mild steel reflux test. The results are shown in Table 8.

TABLE 8
STABILITY TEST RESULTS

| COMPOSITION | pH/TITER INITIAL | FEDERAL ACCELERATED OXIDATION TEST pH/TITER | MILD STEEL REFLUX TEST pH/TITER | APHA COLOR |
|---|---|---|---|---|
| Control | 6.9/<0.1 | 3.1/15.4 | 6.9/<0.1 | 90 |
| Stabilized | 6.9/<0.1 | 6.5/0.2 | 7.2/0.1 | 21 |

EXAMPLE VI

A first composition is prepared by admixing 954.1 grams of trichloroethylene containing 0.01 percent thymol with 3.9 grams of an 80 percent 2-methylene-1,3- dioxolane composition wherein the chief impurity is 2-chloromethyl-1,3-dioxolane, 1.2 grams n-propanol and 0.24 gram of 40 percent acetaldehyde dimethylhydrazone in trichloroethylene.

A second composition is prepared by admixing 796.5 grams of trichloroethylene containing 0.01 percent thymol with 1.0 gram n-propanol, 0.2 gram of 40 percent acetaldehyde dimethylhydrazone in trichloroethylene and 8.1 grams of the additive composition of Example V.

The first composition and the second composition are tested according to the pH/titer test, the Federal Accelerated Oxidation test and the standard stability test. The results are shown in Table 9.

TABLE 9
STABILITY TEST RESULTS

| COMPO-SITION | pH/TITER INITIAL | FEDERAL ACCELERATED OXIDATION TEST pH/TITER | STANDARD STABILITY TEST pH/TITER |
|---|---|---|---|
| First | 7.3/0.2 | 8.4/0.2 | 6.8/<0.1 |
| Second | 7.1/<0.1 | 8.2/0.5 | 6.9/— |

EXAMPLE VII

A trichloroethylene control composition is prepared containing 0.01 percent thymol, 0.125 percent n-propanol and 0.01 percent acetaldehyde dimethylhydrazone.

An additive composition is prepared containing about 21 percent 2-methylene-1,3-dioxolane, about 5 percent 2-chloromethyl-1,3-dioxolane and about 74 percent trichloroethylene.

A first composition is prepared by admixing 1319.4 grams trichloroethylene containing 0.01 percent thymol with 1.7 grams n-propanol and 26.9 grams of the above additive composition.

A second composition is prepared by admixing 100 parts of the first composition and 0.01 part acetaldehyde dimethylhydrazone.

The first composition, the second composition and the control composition are tested as shown in Table 10, which also shows the results obtained.

TABLE 10
STABILITY TEST RESULTS

| TEST | COMPOSITION First | Second | Control |
|---|---|---|---|
| Mild Steel Reflux | | | |
| pH/titer | 6.8/0.1 | 7.0/— | 3.2/13.4 |
| Metal Condition | | | |
| Vapor Phase | Clean | Clean | Rusty |
| Interface | Clean | Clean | Rusty |
| Liquid Phase | Slight white film with iridescence | Clean | Rusty |
| Solvent Appearance (APHA) | 6 | 9 | 500 (very cloudy) |
| Federal Accelerated Oxidation | | | |
| pH/titer | 3.8/10.9 | 6.6/0.2 | 3.5/20.4 |
| Strip Condition | | | |
| Flask | Clean | Clean | Tarnished |
| Condenser | Very black and rusty | Clean | Clean |
| Solvent Appearance (APHA) | 2650 (dark red-orange) | 200 (slightly cloudy) | >500 (cloudy) |
| Standard Stability | | | |
| pH/titer | | 6.8/<0.1 | Not run |
| AgNO$_3$ Trap Condition | Clear | | Not run |
| Solvent Appearance | Dark red-amber | | |

Although the recent invention has been described with reference to specific details of certain embodiments thereof, it is not intended that such detail should be regarded as limitations upon the scope of the invention except insofar as they are included in the accompanying claims.

I claim:

1. Solvent composition comprising:
   a. a member selected from the group consisting of methylchloroform, trichloroethylene and a mixture thereof; and
   b. a corrosion inhibiting amount of acid acceptor represented by the structural formula

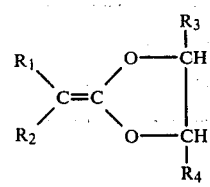

wherein $R_1$ and $R_2$ are each independently hydrogen, methyl or ethyl and wherein $R_3$ and $R_4$ are each independently hydrogen or alkyl containing from 1 to about 6 carbon atoms.

2. The solvent composition of claim 1 wherein said member constitutes from about 85 percent to about 99.99 percent by weight of said solvent composition, and wherein said acid acceptor constitutes from about 0.01 percent to about 10 percent by weight of said solvent composition.

3. The solvent composition of claim 1 wherein $R_1$ and $R_2$ are both hydrogen.

4. The solvent composition of claim 1 wherein $R_3$ and $R_4$ are each independently hydrogen or lower alkyl containing from 1 to about 4 carbon atoms.

5. The solvent composition of claim 1 wherein $R_3$ and $R_4$ are each independently hydrogen, methyl or ethyl.

6. The solvent composition of claim 1 wherein $R_3$ and $R_4$ are both hydrogen.

7. The solvent composition of claim 1 wherein said acid acceptor is 2-methylene-1,3-dioxolane.

8. The solvent composition of claim 1 wherein said member is trichloroethylene.

9. The solvent composition of claim 8 which also contains at least one of the following: aromatic compound having a phenolic hydroxyl group and having a normal boiling temperature in the range of from about 180° C. to about 250° C., saturated aliphatic monoepoxide containing from about 3 to about 8 carbon atoms, saturated cycloaliphatic monoepoxide containing from about 6 to about 8 carbon atoms, alkanol containing from 1 to about 8 carbon atoms and aliphatic aldehyde hydrazone having from 1 to about 7 carbon atoms wherein no aliphatic group has more than about 4 carbon atoms.

10. The solvent composition of claim 1 wherein said member is methylchloroform.

11. The solvent composition of claim 10 which also contains at least one of the following: nitroalkane having from 1 to about 3 carbon atoms, saturated aliphatic monoepoxide containing from about 3 to about 8 carbon atoms, saturated cycloaliphatic monoepoxide containing from about 6 to about 8 carbon atoms, 1,4-dioxane, 1,3-dioxolane containing up to two alkyl substituents, each of the alkyl substituents having from 1 to 2 carbon atoms, acetone, methyl ethyl ketone, methyl isopropyl ketone, diethyl ketone, acetonitrile, propionitrile, acrylonitrile, an alkynol having from 3 to about 12 carbon atoms, an alkanol having from 1 to about 8 carbon atoms, dimethyoxymethane, aliphatic aldehyde hydrazone having from 1 to about 7 carbon atoms wherein no aliphatic group has more than about 4 carbon atoms, and toluene.

* * * * *